(12) United States Patent
Li et al.

(10) Patent No.: US 12,161,511 B2
(45) Date of Patent: Dec. 10, 2024

(54) MASK POSITIONING ASSEMBLY AND POSITIONING SYSTEM

(71) Applicant: OUR UNITED CORPORATION, Xi'an (CN)

(72) Inventors: Daliang Li, Xi'an (CN); Hao Yan, Xi'an (CN); Hui Liu, Xi'an (CN); Fangzheng Chen, Xi'an (CN); Peng Zan, Xi'an (CN); Jinsheng Li, Xi'an (CN); Zhongyuan Zhang, Xi'an (CN); Deping Chen, Xi'an (CN)

(73) Assignee: OUR UNITED CORPORATION, Xi'an (CN)

( * ) Notice: Subject to any disclaimer, the term of this patent is extended or adjusted under 35 U.S.C. 154(b) by 396 days.

(21) Appl. No.: 17/629,706

(22) PCT Filed: Jul. 22, 2019

(86) PCT No.: PCT/CN2019/097113
§ 371 (c)(1),
(2) Date: Jan. 24, 2022

(87) PCT Pub. No.: WO2021/012152
PCT Pub. Date: Jan. 28, 2021

(65) Prior Publication Data
US 2022/0280258 A1  Sep. 8, 2022

(51) Int. Cl.
*A61B 90/18*       (2016.01)
*A61N 5/10*        (2006.01)

(52) U.S. Cl.
CPC ............ *A61B 90/18* (2016.02); *A61N 5/10* (2013.01); *A61N 2005/1097* (2013.01)

(58) Field of Classification Search
CPC ... A61B 90/18; A61N 5/10; A61N 2005/1097
See application file for complete search history.

(56) References Cited

U.S. PATENT DOCUMENTS

| | | |
|---|---|---|
| 5,702,406 A | 12/1997 | Vilsmeier et al. |
| 2004/0015176 A1 | 1/2004 | Cosman |
| 2006/0002511 A1 | 1/2006 | Miller et al. |

(Continued)

FOREIGN PATENT DOCUMENTS

| | | |
|---|---|---|
| CN | 1894577 A | 1/2007 |
| CN | 101574264 A | 11/2007 |

(Continued)

OTHER PUBLICATIONS

International search report of PCT application No. PCT/CN2019/097113 issued on Apr. 23, 2020.

(Continued)

*Primary Examiner* — Nicole M Ippolito
(74) *Attorney, Agent, or Firm* — Knobbe Martens Olson & Bear LLP

(57) ABSTRACT

A mask positioning assembly is provided. The mask positioning assembly includes a cradle frame, an adapter frame, and a positioning mask. The cradle frame is connected to both the adapter frame and the positioning mask. The adapter frame can be configured to be connected to any of positioning assembly support frames in different types of positioning systems. A positioning system is also provided.

18 Claims, 9 Drawing Sheets

(56) References Cited

U.S. PATENT DOCUMENTS

| | | |
|---|---|---|
| 2009/0260636 A1 | 10/2009 | Markstroem |
| 2010/0268248 A1 | 10/2010 | Hong |
| 2012/0288820 A1* | 11/2012 | Choe .................... A61B 5/4542 |
| | | 433/29 |
| 2016/0317243 A1 | 11/2016 | Garcia Coni et al. |
| 2018/0008840 A1 | 1/2018 | Van Voorst et al. |
| 2018/0235824 A1 | 8/2018 | Nordgren et al. |
| 2019/0038377 A1 | 2/2019 | Wortmann et al. |
| 2020/0345572 A1 | 11/2020 | Cooke et al. |
| 2021/0016110 A1 | 1/2021 | Gou et al. |

FOREIGN PATENT DOCUMENTS

| | | |
|---|---|---|
| CN | 101564575 A | 10/2009 |
| CN | 202620501 U | 12/2012 |
| CN | 205460496 U | 8/2016 |
| CN | 205795976 U | 12/2016 |
| CN | 108211139 A | 6/2018 |
| CN | 207837652 U | 9/2018 |
| CN | 108635681 A | 10/2018 |
| CN | 109068993 A | 12/2018 |
| CN | 109152618 A | 1/2019 |
| CN | 109621232 A | 4/2019 |
| CN | 208973882 U | 6/2019 |
| DE | 4432891 A1 | 3/1996 |
| EP | 2870940 A1 | 5/2015 |

OTHER PUBLICATIONS

First office action of Chinese application No. 201980088104.3 issued on Oct. 28, 2023, which is foreign counterpart application of this US application.

China National Intellectual Property Administration, Notification to grant patent right for invention of Chinese application No. 201980088104.3 issued on May 14, 2024, which is foreign counterpart application of this US application.

* cited by examiner

MASK POSITIONING ASSEMBLY AND POSITIONING SYSTEM

CROSS-REFERENCE TO RELATED APPLICATION

This application is a U.S. national stage of international application No. PCT/CN2019/097113, filed on Jul. 22, 2019, the disclosure of which is herein incorporated by reference in its entirety.

TECHNICAL FIELD

The present disclosure relates to the field of radiotherapy technologies, and in particular to a mask positioning assembly and a positioning system.

BACKGROUND

Before performing radiotherapy to a target point in a patient's head, the target point needs to be imaged using an image acquisition system to acquire an image of the target point. After that, a treating physician may make a treatment plan based on the image of the target point. Finally, according to the treatment plan, radiotherapy may be performed to the target point using a radiotherapy system.

SUMMARY

The present disclosure provides a mask positioning assembly and a positioning system. The technical solution is as follows.

In a first aspect, a mask positioning assembly is provided. The mask positioning assembly includes a cradle frame, an adapter frame, and a positioning mask, wherein the cradle frame is connected to both the adapter frame and the positioning mask, and the adapter frame is configured to be connected to any of positioning assembly support frames in different types of positioning systems.

In a second aspect, a positioning system is provided. The positioning system includes a patient support device, a positioning assembly support frame, and the mask positioning assembly as defined in the above aspect, wherein the positioning assembly support frame is fixedly disposed on the patient support device, and the mask positioning assembly is connected to the positioning assembly support frame.

BRIEF DESCRIPTION OF THE DRAWINGS

For clearer descriptions of the technical solutions in the embodiments of the present disclosure, the following briefly introduces the accompanying drawings required for describing the embodiments. Apparently, the accompanying drawings in the following description show merely some embodiments of the present disclosure, and a person of ordinary skill in the art may still derive other drawings from these accompanying drawings without creative efforts.

DETAILED DESCRIPTION

For clearer descriptions of the objectives, technical solutions, and advantages of the present disclosure, embodiments of the present disclosure are described in detail hereinafter with reference to the accompanying drawings.

Currently, an image acquisition system may usually include computed tomography (CT) equipment or magnetic resonance imaging (MRI) equipment. A CT image of a target point in a patient's head may be acquired by imaging the target point in the patient's head using an image acquisition system including CT equipment. An MRI image of the target point in the patient's head may be acquired by imaging the target point in the patient's head using an image acquisition system including the MRI equipment. After the CT image or MRI image is acquired, the treating physician may make a treatment plan. According to the treatment plan, radiotherapy is performed on the target point in the patient's head using a radiotherapy system including radiotherapy equipment.

In the related art, in order to ensure that the patient's head is not moved during image acquisition process for the target point in the patient's head and the radiotherapy process, the patient's head usually needs to be fixed using a mask positioning assembly.

However, due to structural differences between various equipment in different types of positioning systems such as the image acquisition system and the radiotherapy system, the patient's head needs to be positioned using different mask positioning assemblies during the image acquisition process for the target point in the patient's head and the radiotherapy process, which has a low positioning accuracy, and causes high cost and low efficiency.

Figure 1:
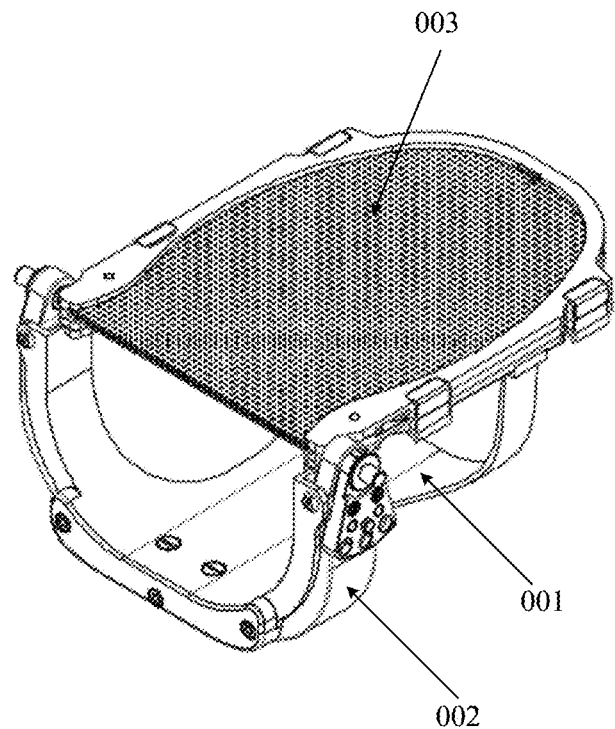
FIG. 1 is a schematic structural diagram of a mask positioning assembly according to an embodiment of the present disclosure.

FIG. 1 is a schematic structural diagram of a mask positioning assembly according to an embodiment of the present disclosure. The mask positioning assembly can solve the problems of low positioning accuracy, high cost, and low efficiency of the mask positioning assembly in the related art. As may be seen with reference to FIG. 1, the mask positioning assembly may include a cradle frame 001, an adapter frame 002, and a positioning mask 003.

The cradle frame 001 may be connected to both the adapter frame 002 and the positioning mask 003. The positioning mask 003 may be configured to position a patient's head, to ensure that the patient's head does not move during image acquisition and radiotherapy.

The adapter frame 002 may be configured to be connected to any of positioning assembly support frames in different types of positioning systems, such that in the case that the patient is treated with different types of positioning systems, the patient's head may be positioned using the same mask positioning assembly, which has a low cost, and there is no need to frequently replace different mask positioning assemblies to adapt to different positioning systems, which is highly efficient.

In an exemplary embodiment, during imaging of a target point in the patient's head using an image acquisition system and radiotherapy treatment for the target point in the patient's head using a radiotherapy system, the patient's head may be positioned using the mask positioning assembly according to the embodiment of the present disclosure.

In summary, the embodiments of the present disclosure provide a mask positioning assembly, which may include a cradle frame, an adapter frame, and a positioning mask, wherein the cradle frame may be connected to both the adapter frame and the positioning mask, and the adapter frame may be configured to be connected to any of positioning assembly support frames in different types of positioning systems. Therefore, the mask positioning assembly may be applicable to different types of positioning systems, and the patient's head may be positioned quickly and accurately, which has a low cost. In addition, there is no need to frequently replace different mask positioning assemblies to adapt to different positioning systems, which causes a high efficiency. In addition, by positioning the patient's head using the mask positioning assembly according to the embodiments of the present disclosure, the problem of poor positioning accuracy can be avoided in the case that the patient is positioned using different mask positioning assemblies, therefore a high positioning accuracy is achieved and the patient's therapeutic effect is improved.

Optionally, the different types of positioning systems may include at least two of an image acquisition system including CT equipment, an image acquisition system including MRI equipment, and a radiotherapy system.

In an exemplary embodiment, the adapter frame 002 may be adapted to the image acquisition system including CT equipment, the image acquisition system including MRI equipment, and the radiotherapy system.

Figure 2:
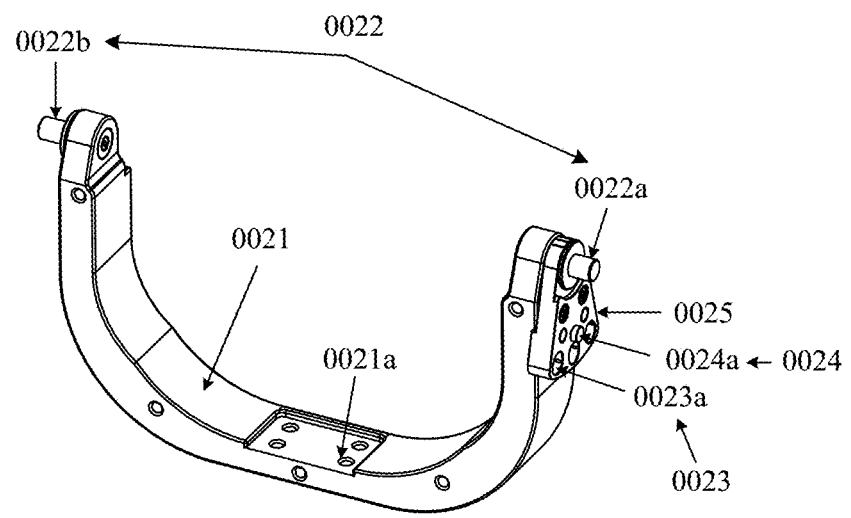
FIG. 2 is a schematic structural diagram of an adapter frame according to an embodiment of the present disclosure.

FIG. 2 is a schematic structural diagram of an adapter frame according to an embodiment of the present disclosure. As may be seen with reference to FIG. 2, the adapter frame 002 may include a first frame 0021 and a first connecting structure 0022 disposed on the first frame 0021.

As may be seen with reference to FIG. 2, a first connecting port 0021a may be disposed on the first frame 0021, wherein the first frame 0021 may be connected to the cradle frame 001 through the first connecting port 0021a. The first connecting structure 0022 may be configured to be connected to a second connecting structure 102 on a second frame 101 of a positioning assembly support frame 10 in a positioning system, wherein the first connecting structure 0022 may be detachably connected to the second connecting structure 102. Thus, a detachable connection between the adapter frame 002 and the positioning assembly support frame 10 may be achieved In an embodiment of the present disclosure, as shown in FIG. 2, the first connecting structure 0022 may include a first connecting substructure 0022a and a second connecting substructure 0022b respectively disposed at two ends of the first frame 0021. The first connecting substructure 0022a may be configured to be connected to a third connecting substructure 102a of the second connecting structure 102, and the second connecting substructure 0022b may be configured to be connected to a fourth connecting substructure 102b of the second connecting structure 102. As may be seen with reference to FIGS. 3 and 4, the third connecting substructure 102a and the fourth connecting substructure 102b may be respectively disposed at two ends of the second frame 101.

Figure 3:
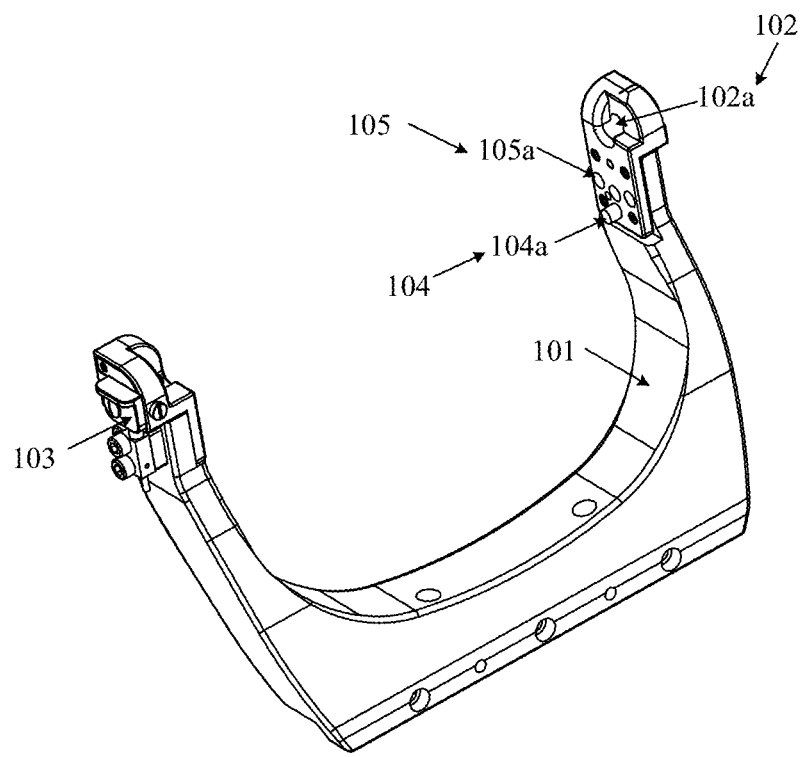
FIG. 3 is a schematic structural diagram of a positioning assembly support frame according to an embodiment of the present disclosure.
Figure 4:
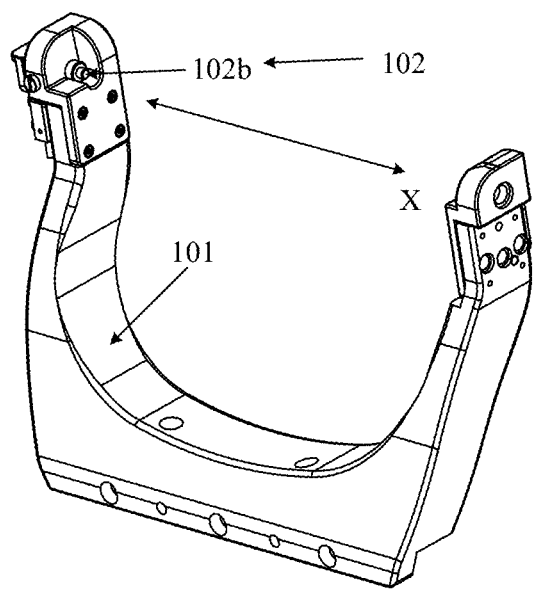
FIG. 4 is a schematic structural diagram of another positioning assembly support frame according to an embodiment of the present disclosure.
Figure 5:
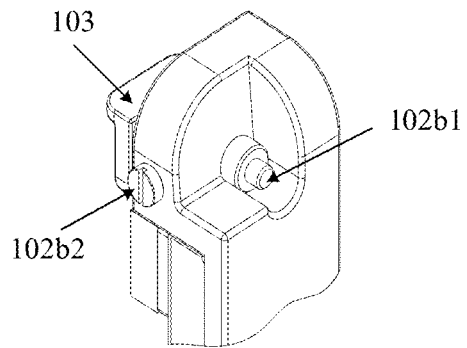
FIG. 5 is a partial structural diagram of the positioning assembly support frame shown in FIG. 4.

FIG. 5 is a partial structural diagram of the positioning assembly support frame shown in FIG. 4. As may be seen with reference to FIGS. 2 to 5, the first connecting substructure 0022a may be a first connecting rod, the third connecting substructure 102a may be a through hole, and the first connecting substructure 0022a may be connected to the third connecting substructure 102a by inserting the first connecting rod 0022a into the through hole. The second connecting substructure 0022b may be a second connecting rod, and the fourth connecting substructure 102b may include a stepped boss, wherein the stepped boss 102b1 may be movable relative to the second frame 101 in an axial direction X of the stepped boss 102b1.

With reference to FIGS. 3 to 5, the stepped boss 102b1 may include two coaxial bosses with different diameters. A through hole may be provided on the second frame 101. One end of a boss with a larger diameter of the stepped boss 102b1 is connected to a boss with a smaller diameter, and the other end of the boss with a larger diameter may pass through the through hole. For example, with reference to FIG. 3, the positioning assembly support frame 10 may further include a knob 103 which may be fixedly connected to the other end of the boss with a larger diameter of the stepped boss 102b1. Therefore, an operator may turn the knob 103 to make the stepped boss 102b1 move in the axial direction X.

In an alternative embodiment, the fourth connecting substructure 102b is also a through hole, and the second connecting rod 0022b may be inserted into the through hole, thereby connecting the second connecting rod 0022b to the positioning assembly support frame.

In another alternative embodiment, both the first connecting substructure 0022a and the second connecting substructure 0022b may be through holes, and both the third connecting substructure 102a and the fourth connecting substructure 102b may be connecting rods, then the adapter frame 002 is connected to the positioning assembly support frame 10 by inserting the third connecting substructure 102a into the first connecting substructure 0022a, and inserting the fourth connecting substructure 102b into the second connecting substructure 0022b.

In an embodiment of the present disclosure, the first frame 0021 is lockable by the connection between the third connecting substructure 102a and the first connecting substructure 0022a and/or connection between the fourth connecting substructure 102b and the second connecting substructure 0022b, such that a position of the first frame 0021 is fixed relative to the second frame 101.

As may be seen with reference to FIG. 2, the adapter frame 002 may further include a first angle adjusting mechanism 0023 and/or a first angle detecting mechanism 0024 disposed on the first frame 0021. For example, the structure shown in FIG. 2 includes the first angle adjusting mechanism 0023 and the first angle detecting mechanism 0024.

Referring to FIG. 3, the first angle adjusting mechanism 0023 is configured to adjust an angle between the first frame 0021 and the second frame 101 by cooperation with a second angle adjusting mechanism 104 on the second frame 101. The first angle detecting mechanism 0024 may be configured to detect the angle between the first frame 0021 and the second frame 101 by cooperation with a second angle detecting mechanism 105 on the second frame 101.

Optionally, as shown in FIG. 2, the first angle adjusting structure 0023 may include at least two second connecting ports 0023a the positions of which may be fixed relative to the first frame 0021. For example, FIG. 2 shows three second connecting ports 0023a. The second angle adjusting structure 104 may include a first connecting shaft 104a. A target second connecting port in the at least two second connecting ports 0023a may be configured to be connected to the first connecting shaft 104a of the second angle adjusting mechanism 104, such that the angle of the first frame relative to the second frame 101 is adjusted to an angle corresponding to the target second connecting port.

By connecting different second connecting ports 0023a with the first connecting shaft 104a in the positioning assembly support frame 10, the angle between the first frame 0021 of the adapter frame 002 and the second frame 101 of the positioning assembly support frame 10 may be adjusted, such that during radiotherapy, it is convenient to adjust the angle of the patient's head, and radiotherapy can be performed on the target point in the patient's head from different angles using the radiotherapy system.

The first angle detecting mechanism 0024 may include a second connecting shaft 0024a the position of which may be fixed relative to the first frame 0021. The second angle detecting mechanism 105 may include at least two third connecting ports 105a. The second connecting shaft 0024a may be configured to be connected to a target third connecting port in the at least two third connecting ports 105a of the second angle detecting mechanism 105, to trigger an angle detector in the target third connecting port to detect the angle of the first frame 0021 relative to the second frame 101.

In an embodiment of the present disclosure, each of the third connecting ports 105a may be provided with an angle detector, wherein the angle detector may be a proximity switch. In the case that the first connecting shaft 104a on the positioning assembly support frame 10 is connected to one of the second connecting ports 0023a, the second connecting shaft 0024a may be connected to the target third connecting port. The proximity switch in the target third connecting port connected to the second connecting shaft 0024a may send a positioning signal to an upper computer in the positioning system, and then the upper computer may determine the angle between the first frame 0021 of the adapter frame 002 and the second frame 101 of the positioning assembly support frame 10 based on the position of the target third connecting port in which the proximity switch that sends the positioning signal is disposed.

Optionally, the at least two second connecting ports 0023a may be disposed on the first frame 0021. In an alternative embodiment, with reference to FIG. 2, the adapter frame 002 may further include a connecting plate 0025 which may be fixedly connected to the first frame 0021, wherein the at least two second connecting ports 0023a may be disposed on the connecting plate 0025. The second connecting shaft 0024a may also be disposed on the connecting plate 0025. The second connecting shaft 0024a may be perpendicular to the plate face of the connecting plate 0025.

In an embodiment of the present disclosure, the connecting plate 0025 may be fan-shaped, and a top corner of the fan shape may be a rounded corner. A through hole may be disposed at one end, proximal to the top corner, on the connecting plate 0025. The connecting plate 0025 may be sleeved on the first connecting substructure 0022a (e.g., the first connecting rod on the right side of FIG. 2) via the through hole. In addition, in order to ensure that the connection between the connecting plate 0025 and the first frame 0021 is reliable, the connecting plate 0025 and the first frame 0021 may be further fixedly connected to each other by bolts and positioning pins.

Optionally, both the second connecting port 0023a and the third connecting port 105a may be round holes, wherein an axis of each of the round holes may be parallel to the first connecting shaft 104a and the second connecting shaft 0024a. Both the first connecting shaft 104a on the positioning assembly support frame and the second connecting shaft 0024a on the connecting plate 0025 may be rod-shaped structures.

Figure 6:
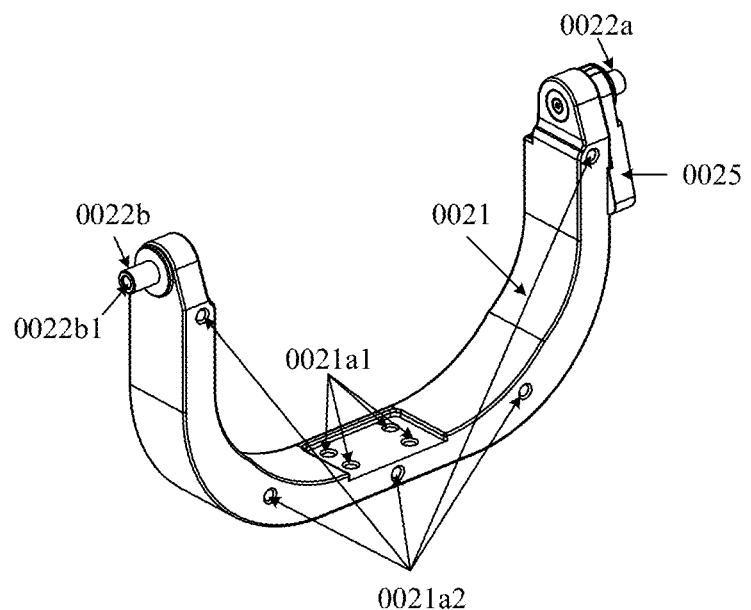
FIG. 6 is a schematic structural diagram of another adapter frame according to an embodiment of the present disclosure.

FIG. 6 is a schematic structural diagram of another adapter frame according to an embodiment of the present disclosure. As may be seen with reference to FIGS. 2 and 6, the second connecting substructure 0022b (e.g., the second connecting rods on the left in FIGS. 2 and 6) may be provided with a fixing hole 0022b1, wherein the fixing hole 0022b1 may be coaxial with the second connecting rod 0022b. The second connecting rod 0022b may be configured to be sleeved, through the fixing hole 0022b1, on the boss with a smaller diameter of the stepped boss 102b1 in the positioning assembly support frame 10, and an end face of one end of the second connecting rod 0022b may be configured to contact an end face of the boss with a larger diameter of the stepped boss 102b1. The connecting plate 0025 in the adapter frame 002 may be connected to the first connecting rod 0022a.

In an embodiment of the present disclosure, before treatment, one side, where the second connecting shaft 0024a is disposed, of the connecting plate 0025 may be configured to be in contact with one side, where the at least two third connecting ports 105a and the first connecting shaft 104a are disposed, of the positioning assembly support frame 10, and then the position of the stepped boss 102b1 in the axial direction X may be adjusted through the knob 103 to make the boss with a smaller diameter of the stepped boss 102b1 be inserted into the fixing hole 0022b1, and make the end face of the boss with a larger diameter of the stepped boss 102b1 be in contact with one end, distal from the first frame 0021, of the second connecting rod 0022b provided with the fixing hole 0022b1, thereby fixedly connecting the first frame 0021 with the second frame 101. That is, a fixed connection between the adapter frame 002 and the positioning assembly support frame 10 is achieved.

After the treatment is completed, by adjusting the position of the stepped boss 102b1 in the axial direction X through the knob 103, the stepped boss 102b1 moves toward one end distal from the at least two third connecting ports 105a in the axial direction X, and the first frame 0021 is disconnected from the second frame 101. That is, the adapter frame 002 is disconnected from the positioning assembly support frame 10, which facilitates the removal of the mask positioning assembly 10 from the positioning system.

As may be seen with reference to FIGS. 2 and 6, the first frame 0021 may be a U-shaped frame, and the first connecting port 0021a may include a plurality of first connecting holes 0021a1 and a plurality of second connecting holes 0021a2. The plurality of first connecting holes 0021a1 may be disposed at the bottom of the U-shaped frame 0021. For example, the plurality of first connecting holes 0021a1 may be disposed at an inner side of the bottom of the U-shaped frame 0021, and the plurality of first connecting holes 0021a1 may be threaded holes. The plurality of first connecting holes 0021a1 may be configured to connect the bottom of the cradle frame 001. The plurality of second connecting holes 0021a2 may be disposed on an end face of the U-shaped frame 0021, wherein the end face is parallel to the axes of the first connecting hole 0021a1, the first connecting rod 0022a, and the second connecting rod 0022b. The plurality of second connecting holes 0021a2 may be configured to connect the end face of the cradle frame 001. The first connecting rod 0022a and the second connecting rod 0022b in the adapter frame 002 may be respectively disposed at two ends of the U-shaped frame 0021 and both the first connecting rod 0022a and the second connecting rod 0022b are disposed outside the U-shaped frame. Moreover, the first connecting rod 0022a and the second connecting rod 0022b may be coaxial.

The axis of the first connecting hole 0021a1, the axis of the second connecting hole 0021a2, and the axis of the connecting rod 0022 may be perpendicular to each other.

As may be seen with reference to FIG. 6, the first connecting port 0021a may include four first connecting holes 0021a1 and five second connecting holes 0021a2. Among the five second connecting holes 0021a2, three of the second connecting holes 0021a2 may be disposed on the end face of the bottom of the first frame 0021, and the other two second connecting holes 0021a2 may be disposed on the end faces of two ends of the first frame 0021.

It should be noted that the first connecting port 0021a may also include only two first connecting holes 0021a1 or only three second connecting holes 0021a2. The number of the first connecting holes 0021a1 and the second connecting holes 0021a2 included in the first connecting port 0021a is not limited in the embodiments of the present disclosure, as long as the adapter frame 002 and the cradle frame 001 is connected tightly.

Figure 7:
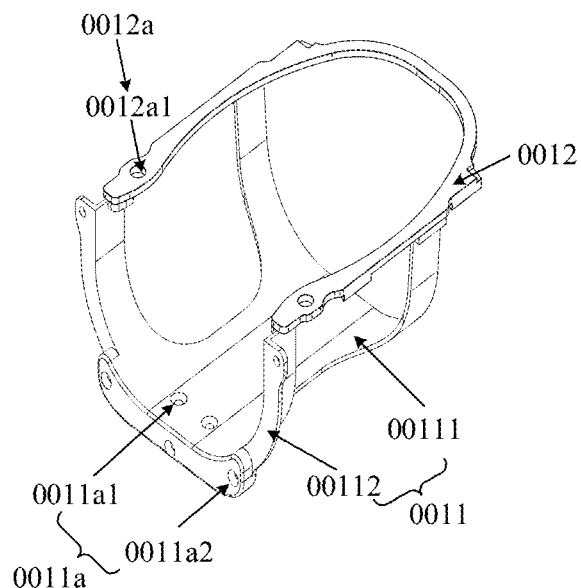
FIG. 7 is a schematic structural diagram of a cradle frame according to an embodiment of the present disclosure.

FIG. 7 is a schematic structural diagram of a cradle frame according to an embodiment of the present disclosure. As may be seen with reference to FIG. 7, the cradle frame 001 may include an arc-shaped support plate 0011 and a positioning plate 0012 connected to the arc-shaped support plate 0011. The arc-shaped support plate 0011 may be connected to the adapter frame 002, and the positioning plate 0012 may be connected to the positioning mask 003.

With reference to FIG. 7, the arc-shaped support plate 0011 may be provided with a fourth connecting port 0011a through which the arc-shaped support plate 0011 may be connected to the adapter frame 002. The positioning plate 0012 may be provided with a fifth connecting port 0012a through which the positioning plate 0012 may be connected to the positioning mask 003.

With reference to FIG. 7, the arc-shaped support plate 0011 may include an arc-shaped frame 00111 and a fixing plate 00112 connected to one end of the arc-shaped frame 00111. The fixing plate 00112 may be perpendicular to the positioning plate 0012. As may be seen from FIG. 7, the arc-shaped frame 00111 may be in an arc shape that matches the shape of the patient's head. In addition, in order to reduce the overall weight of the mask positioning assembly, a plurality of holes may be formed on the arc-shaped frame 00111.

Optionally, the arc-shaped frame 00111 and the fixing plate 00112 may be connected to each other by bolts, and the arc-shaped frame 00111 and the positioning plate 0012 may also be connected to each other by bolts. In an alternative embodiment, the arc-shaped frame 00111, the fixing plate 00112, and the positioning plate 0012 may be of an integral structure, which is not limited in the embodiments of the present disclosure.

The fourth connecting port 0011a may include a plurality of third connecting holes 0011a1 disposed at the bottom of the arc-shaped frame 00111 and a plurality of fourth connecting holes 0011a2 disposed on the fixing plate 00112. The arc-shaped frame 00111 may be connected to the adapter frame 002 through the third connecting holes 0011a1 and the first connecting holes 0021a1 in the adapter frame 002. The fixing plate 00112 may be connected to the adapter frame 002 through the fourth connecting holes 0011a2 and the second connecting holes 0021a2 in the adapter frame 002.

In an exemplary embodiment, with reference to FIG. 7, the fixing plate 00112 may be U-shaped, and the fourth connecting port 0011a may include two third connecting holes 0011a1 disposed at the bottom of the arc-shaped frame 00111 and five fourth connecting holes 0011a2 disposed on the fixing plate 00112. Three of the five fourth connecting holes 0011a2 on the fixing plate 00112 may be disposed on the end face of the bottom of the fixing plate 00112, and the other two of the five fourth connecting holes 0011a2 may be disposed on the end faces of two ends of the fixing plate 00112. The end face of the fixing plate 00112 may be parallel to the axis of the third connecting hole 0011a1 and perpendicular to the plate face of the positioning plate 0012.

Optionally, the fixing plate 00112 may include a first part and a second part. The first part may be connected to a bottom end of the arc-shaped frame, and the second part may be connected to a top end of the arc-shaped frame 00111. Three of the five fourth connecting holes 0011a2 disposed on the fixing plate 00112 may be disposed at the first part of the fixing plate 00112, and the other two fourth connecting holes may be disposed at the second part of the fixing plate 00112.

It should be noted that the fourth connecting port 0011a may also include four third connecting holes 0011a1 disposed at the bottom of the arc-shaped frame 00111 and three fourth connecting holes 0011a2 disposed on the fixing plate 00112. The number of the third connecting holes 0011a1 and the number of the fourth connecting holes 0011a2 included in the fourth connecting port 0011a are not limited in the embodiments of the present invention, as long as the cradle frame 001 and the adapter frame 002 can be tightly connected.

Optionally, the fifth connecting port 0012a may include a plurality of first positioning holes 0012a1 disposed on the positioning plate 0012. For example, with reference to FIG. 7, the fifth connecting port 0012a may include two first positioning holes 0012a1 disposed on the positioning plate 0012. The positioning plate 0012 may be connected to the positioning mask 003 through the first positioning holes 0012a1.

For the positioning plate 0012 shown in FIG. 7, the plurality of first positioning holes 0012a1 may all be disposed at one end of the positioning plate 0012. Of course, the plurality of first positioning holes 0012a1 may also be disposed in various areas on the positioning plate 0012.

The axis of the third connecting hole 0011a1 may be perpendicular to the axis of the fourth connecting hole 0011a2 and parallel to the axis of the first positioning hole 0012a1.

Figure 8:
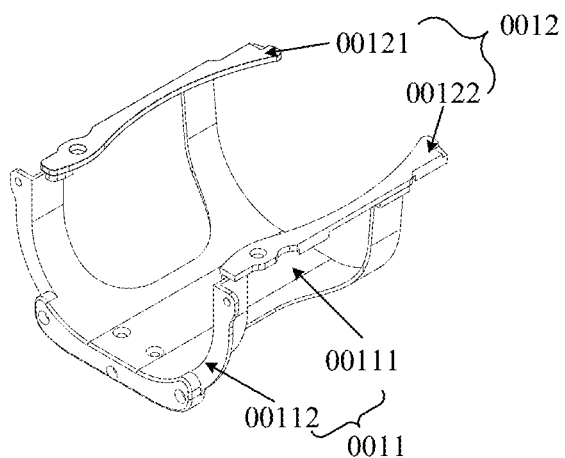
FIG. 8 is a schematic structural diagram of another cradle frame according to an embodiment of the present disclosure.

As may be seen with reference to FIG. 7, the positioning plate 0012 may be U-shaped. In an alternative embodiment, with reference to FIG. 8, the positioning plate 0012 may include a first plate 00121 and a second plate 00122 that are arranged oppositely and not connected to each other. For example, the first plate 00121 and the second plate 00122 may be strip structures with a same shape. The shape of the positioning plate 0012 is not limited in the embodiments of the present disclosure.

In the case that the positioning plate 0012 is U-shaped, that is, the positioning plate 0012 is a U-shaped positioning plate, as shown in FIG. 7, the first positioning holes 0012a1 may be disposed at two ends of the U-shaped positioning plate 0012. That is, the first positioning holes 0012a1 may be disposed at two ends, on a side proximal to the fixing plate 00112, of the U-shaped positioning plate 0012. In an alternative embodiment, the first positioning holes 0012a1 may be disposed at various areas of the U-shaped positioning plate 0012.

In the case that the positioning plate 0012 includes the first plate 00121 and the second plate 00122 that are arranged oppositely, the first positioning holes 0012a1 may be disposed at one end, proximal to the fixing plate 00112, of the first plate 00121 and one end, proximal to the fixing plate 00112, of the second plate 00122. In other words, the first positioning holes 0012a1 may be disposed at one end, proximal to an opening of the positioning mask, of the positioning plate 0012. The opening of the positioning mask is an opening for avoiding the patient's neck.

It should be noted that the cradle frame may further include reinforcing ribs, and by providing the reinforcing ribs, the strength of the cradle frame 001 may be ensured, thereby ensuring the positioning effect of the mask positioning assembly.

Figure 9:
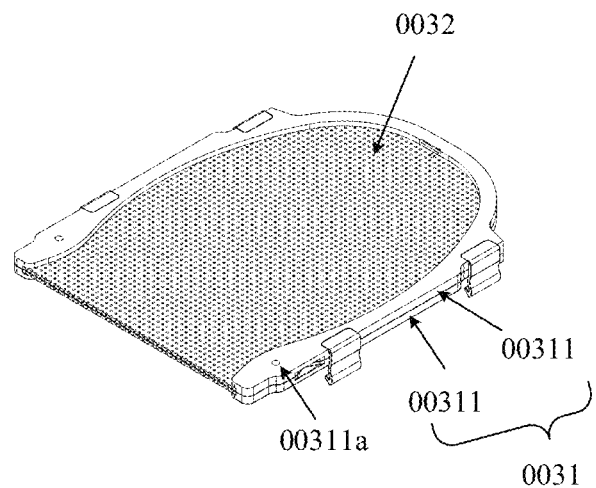
FIG. 9 is a schematic structural diagram of a positioning mask according to an embodiment of the present disclosure.

FIG. 9 is a schematic structural diagram of a positioning mask according to an embodiment of the present disclosure. As may be seen with reference to FIG. 9, the positioning mask 003 may include a mask frame 0031 and a double-shell mask 0032.

The mask frame 0031 may include two mask frame members 00311 fixedly connected to the double-shell mask 0032. The two mask frame members 00311 may be stacked and both fixedly connected to the cradle frame 001. The double-shell mask 0032 may include two masks, each of which may be fixedly connected to a corresponding mask frame member 00311. During image acquisition and radiotherapy, one mask of the double-shell mask 0032 may be disposed under the patient's head, and the other mask may cover the patient's face. The double-shell mask 0032 may fix the patient's head in the positioning system. During positioning of the patient's head, the patient's head may be placed on one mask, and the mask is shaped based on the patient's skull. Then, another mask may be configured to cover the patient's face, and the another mask is shaped based on the patient's face, such that the patient's head is fixed in the positioning system through the double-shell mask 0032.

Optionally, the mask frame member 00311 and the cradle frame 001 may be connected to each other by one or more of a pin, a buckle, and an expansion plug.

Figure 10:
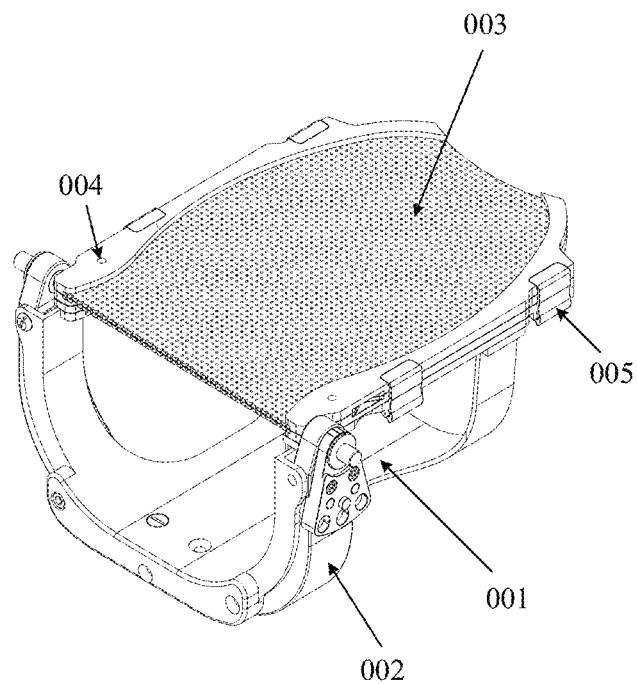
FIG. 10 is a schematic structural diagram of another mask positioning assembly according to an embodiment of the present disclosure.

In an exemplary embodiment, FIG. 10 is a schematic structural diagram of another mask positioning assembly according to an embodiment of the present disclosure. As may be seen with reference to FIG. 10, the mask positioning assembly may further include a pin 004 and a buckle 005. As may be seen with reference to FIGS. 1, 9, and 10, a second positioning hole 00311a corresponding to the first positioning hole 0012a1 on the cradle frame 001 may be disposed on one end, proximal to an opening of the mask frame member, of each mask frame member 00311. The pin 004 may pass through the first positioning hole 0012a1 and the second positioning hole 00311a to connect the mask frame member 00311 with the cradle frame 001. The buckle 005 may be respectively connected to one end, distal from the opening of the mask frame member, of the mask frame member 00311 and the cradle frame 001.

By connecting the mask frame member 00311 to the cradle frame 001 using the pin 004 and the buckle 005, the width of the mask frame member 00311 may be reduced, such that in the case that radiotherapy is performed on the patient's head through the treatment cavity, the range that the radiotherapy system can perform radiotherapy can be increased, and the therapeutic effect can be improved.

In an alternative embodiment, the mask positioning assembly may include a pin and an expansion plug. The mask frame 0031 and the cradle frame 001 may be fixedly connected to each other by the pin and the expansion plug.

Figure 11:
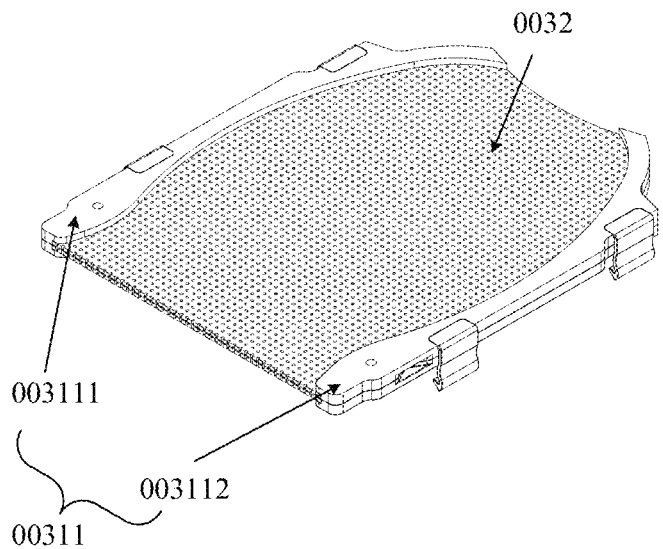
FIG. 11 is a schematic structural diagram of another positioning mask according to an embodiment of the present disclosure.

As may be seen with reference to FIGS. 1 and 9, each mask frame member 00311 may be U-shaped. In an alternative embodiment, with reference to FIGS. 10 and 11, each mask frame member 00311 may include a first frame member 003111 and a second frame member 003112 that are arranged oppositely and not connected to each other. For example, the first frame member 003111 and the second frame member 003112 may be strip structures with a same shape. The shape of the mask frame member 00311 is not limited in the embodiments of the present disclosure.

In the case that each mask frame member 00311 includes the first frame member 003111 and the second frame member 003112 that are arranged oppositely, the positioning plate 0012 may correspondingly include the first plate 00121 and the second plate 00122 that are arranged oppositely, the first frame member 003111 may be connected to the corresponding first plate 00121, and the second frame member 003112 may be connected to the corresponding second plate 00122.

By arranging the mask frame member 00311 to be a structure including the first frame member 003111 and the second frame member 003112, the area covered by the double-shell mask 0032 of the patient's head may be increased, thereby further ensuring that the patient's head does not move. In addition, the area where the radiotherapy system can perform radiotherapy may be further increased.

As may be seen with reference to FIGS. 1, and 9 to 11, two second positioning holes 00311a may be disposed at one end, proximal to the opening of the mask frame member, of each mask frame member 00311. Accordingly, the mask positioning assembly may include two pins 004 and four buckles 005. Of course, the mask positioning assembly may also include other numbers of pins 004 and buckles 005, which are not limited in the embodiments of the present disclosure.

It should be noted that one end of the buckle 005 may be fixedly connected to one mask frame member 00311, distal from the cradle frame 001, of the mask frame 0031, and the other end of the buckle 005 may be buckled on the cradle frame 001. In an alternative embodiment, one end of the buckle 005 may be fixedly connected to the cradle frame 001, and the other end of the buckle 005 may be buckled on one mask frame member 00311, distal from the cradle frame 001, of the mask frame 0031, which is not limited in the embodiments of the present disclosure, as long as the positioning mask 003 can be fixedly connected to the cradle frame 001.

In summary, embodiments of the present disclosure provide a mask positioning assembly, which may include a cradle frame, an adapter frame, and a positioning mask, wherein the cradle frame may be connected to both the adapter frame and the positioning mask, and the adapter frame may be configured to be connected to any of positioning assembly support frames in different types of positioning systems. Therefore, the mask positioning assembly may be applicable to different types of positioning systems, and the patient's head may be positioned quickly and accurately, which has a low cost. There is no need to frequently replace different mask positioning assemblies to adapt to different positioning systems, thereby achieving high efficiency. In addition, by using the mask positioning assembly as defined in the embodiments of the present disclosure to position the patient's head, the problem of poor positioning accuracy in the case that the patient is positioned with different mask positioning assemblies can be avoided, therefore a high positioning accuracy is achieved and a therapeutic effect for the patient is improved.

Figure 12:
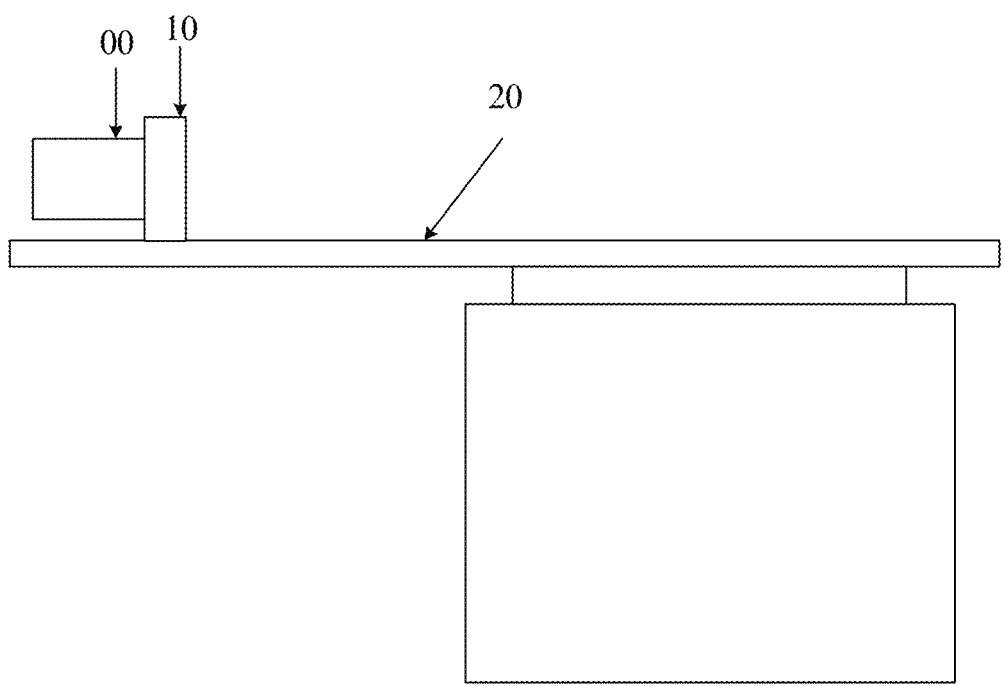
FIG. 12 is a schematic structural diagram of a positioning system according to an embodiment of the present disclosure.

FIG. 12 is a schematic structural diagram of a positioning system according to an embodiment of the present disclosure. As may be seen with reference to FIG. 12, the positioning system may include a patient support device 20, a positioning assembly support frame 10, and the mask positioning assembly 00 as defined in the above embodiments.

Figure 13:
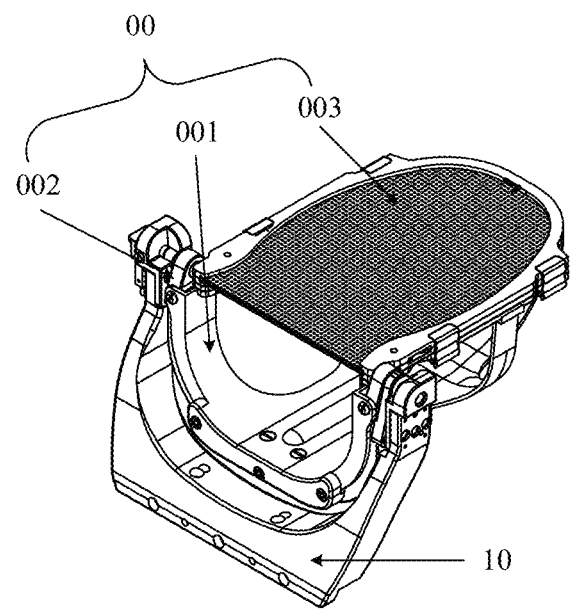
FIG. 13 is a structural schematic diagram of a positioning assembly support frame and a mask positioning assembly according to an embodiment of the present disclosure.

FIG. 13 is a schematic structural diagram of a positioning assembly support frame and a mask positioning assembly according to an embodiment of the present disclosure. With reference to FIGS. 12 and 13, the positioning assembly support frame 10 may be fixedly disposed on the patient support device 20, and the mask positioning assembly 00 may be connected to the positioning assembly support frame 10. The patient support device 20 may be a bed or a seat that supports a patient, such as a treatment couch, a diagnosis couch, a treatment seat, a diagnosis seat, and the like.

As may be seen with reference to FIGS. 3 to 5, the positioning assembly support frame 10 may include a second frame 101 and a second connecting structure 102 disposed on the second frame 101. The second connecting structure 102 may be connected to the first connecting structure 0022 on the first frame 0021 of the adapter frame 002, wherein the second connecting structure 102 is detachably connected to the first connecting structure 0022.

In an embodiment of the present disclosure, the second connecting structure 102 may include a third connecting substructure 102*a* and a fourth connecting substructure 102*b* disposed at two ends of the second frame 101. The third connecting substructure 102*a* may be connected to the first connecting substructure 0022*a* of the first connecting structure 0022. The fourth connecting substructure 102*b* may be connected to the second connecting substructure 0222*b* of the first connecting structure 0022.

As may be seen with reference to FIG. 3, the third connecting substructure 102*a* may be a through hole. As may be seen with reference to FIGS. 4 and 5, the fourth connecting substructure 102*b* may include a stepped boss 102*b*1 disposed on the second frame 101 and a locking structure 102*b*2. In the case that the locking structure 102*b*2 is locked to the stepped boss 102*b*1, the position of the stepped boss 102*b*1 relative to the second frame 101 is fixed. In the case that the locking structure 102*b*2 is not locked to the stepped boss 102*b*1, the stepped boss 102*b*1 is movable relative to the second frame 101 in an axial direction X of the stepped boss 102*b*1.

Figure 14:
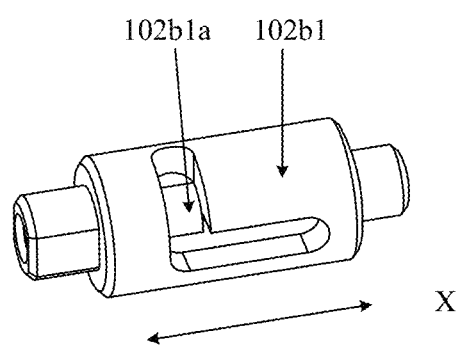
FIG. 14 is a schematic structural diagram of a stepped boss according to an embodiment of the present disclosure.

FIG. 14 is a schematic structural diagram of a stepped boss according to an embodiment of the present disclosure. As may be seen with reference to FIG. 14, the stepped boss 102*b*1 may be provided with an L-shaped groove 102*b*1*a*. One end of the locking structure 102*b*2 may be disposed in the L-shaped groove. In the case that the locking structure 102*b*2 is located in a groove portion, perpendicular to the axial direction X of the stepped boss 102*b*1, of the L-shaped groove 102*b*1*a*, the stepped boss 102*b*1 cannot move along the axial direction X of the stepped boss 102*b*1 relative to the second frame 101 and is fixed relative to the second frame 101, and the locking structure 102*b*2 is locked to the stepped boss 102*b*1. In the case that the locking structure 102*b*2 is located in a groove portion, parallel to the axial direction X of the stepped boss 102*b*1, of the L-shaped groove 102*b*1*a*, the stepped boss 102*b*1 is movable relative to the second frame 101 in the axial direction X of the stepped boss 102*b*1, and the locking structure 102*b*2 is not locked to the stepped boss 102*b*1.

In an embodiment of the present disclosure, by rotating a knob 103 (not shown in FIG. 14) which is fixedly connected to the stepped boss 102*b*1, the locking structure 102*b*2 may be disposed in any of the groove portions with different extending directions of the L-shaped groove 102*b*1*a* on the stepped boss 102*b*1, such that the locking state between the locking structure 102*b*2 and the stepped boss 102*b*1 may be adjusted.

With reference to FIGS. 3 to 5, the stepped boss 102*b*1 may include two coaxial bosses with different diameters. The second frame 101 may be provided with a through hole. One end of the boss with a larger diameter of the stepped boss 102*b*1 is connected to the boss with a smaller diameter, and the other end of the boss with a larger diameter may pass through the through hole.

In an exemplary embodiment, with reference to FIG. 3, the positioning assembly support frame 10 may further include the knob 103 which may be fixedly connected to the other end of the boss with a larger diameter of the stepped boss 102*b*1. An operator may turn the knob 103 to make the stepped boss 102*b*1 move along the axial direction X.

In an alternative embodiment, the fourth connecting substructure 102*b* is also a through hole, and the second connecting rod 0022*b* may be inserted into the through hole, thereby connecting the second connecting rod 0022*b* to the positioning assembly support frame.

In another alternative embodiment, both the third connecting substructure 102*a* and the fourth connecting substructure 102*b* may be connecting rods, and both the first connecting substructure 0222*a* and the second connecting substructure 0022*b* in the adapter frame 002 may be through holes, then the third connecting substructure 102*a* may be inserted into the first connecting substructure 0022*a*, and the fourth connecting substructure 102*b* may be inserted into the second connecting substructure 0022b, thereby connecting the adapter frame 002 to the positioning assembly support frame 10.

In an embodiment of the present disclosure, the first frame 0021 is lockable by the connection between the third connecting substructure 102a and the first connecting substructure 0022a and/or the connection between the fourth connecting substructure 102b and the second connecting substructure 0022b, such that the position of the first frame 0021 relative to the second frame 101 may be fixed.

As may be seen with reference to FIG. 3, the positioning assembly support frame 10 may further include a second angle adjusting mechanism 104 and/or a second angle detecting structure 105 disposed on the second frame 101. For example, the structure shown in FIG. 3 includes the second angle adjusting mechanism 104 and the second angle detecting mechanism 105.

The second angle adjusting mechanism 104 may be configured to adjust an angle between the second frame 101 and the first frame 0021 by cooperation with the first angle adjusting mechanism 0023 on the first frame 0021. The second angle detecting mechanism 105 may be configured to detect the angle between the second frame 101 and the first frame 0021 by cooperation with the first angle detecting mechanism 0024 on the first frame 0021.

Optionally, the second angle adjusting mechanism 104 may include a first connecting shaft 104a, wherein the position of the first connecting shaft 104a may be fixed relative to the second frame 101. The first connecting shaft 104a may be configured to be connected to the target second connecting port in the at least two second connecting ports 0023a in the first angle adjusting structure 0023, such that the angle of the first frame 0021 relative to the second frame 101 may be adjusted to an angle corresponding to the target second connecting port.

By connecting different second connecting ports 0023a to the first connecting shaft 104a in the positioning assembly support frame 10, the angle between the first frame 0021 of the adapter frame 002 and the second frame 101 of the positioning assembly support frame 10 may be adjusted, such that during radiotherapy, it is convenient to adjust the angle of the patient's head, and radiotherapy can be performed on the target point of the patient's head from different angles using the radiotherapy system.

The second angle detecting mechanism 105 may include at least two third connecting ports 105a, wherein the positions of the at least two third connecting ports 105a relative to the second frame 101 are fixed. A target third connecting port in the at least two third connecting ports 105a may be configured to be connected to the second connecting shaft 0024a of the first angle detecting mechanism 0024, to trigger an angle detector in the target third connecting port to detect the angle of the first frame 0021 relative to the second frame 101.

In an embodiment of the present disclosure, each of the third connecting ports 105a may be provided with the angle detector, wherein the angle detector may be a proximity switch. In the case that the first connecting shaft 104a in the positioning assembly support frame 10 is connected to one of the second connecting ports 0023a, the second connecting shaft 0024a may be connected to the target second connecting port. The proximity switch in the target second connecting port 0023a connected to the second connecting shaft 0024a may send a positioning signal to an upper computer in the positioning system, and then the upper computer may determine, based on the position of the target second connecting port where the proximity switch that sends the positioning signal is located in, the angle between the first frame 0021 of the adapter frame 002 and the second frame 101 of the positioning assembly support frame 10.

The third connecting ports 105a and the second connecting ports 0023a in the mask positioning assembly 00 may all be round holes, and the axis of each round hole may be parallel to the first connecting shaft 104a and the second connecting shaft 0024a. Both the first connecting shaft 104a and the second connecting shaft 0024a in the mask positioning assembly 00 may be rod-shaped structures.

Before treatment, one side, where the second connecting shaft 0024a is disposed, of the connecting plate 0025 in the mask positioning assembly 00 is configured to be in contact with one side, where the at least two third connecting ports 105a and the first connecting shaft 104a is disposed, of the positioning assembly support frame 10, then the stepped boss 102b1 may be adjusted in the axial direction X, to make the boss with a smaller diameter of the stepped boss 102b1 enter the fixing hole 0022b1 disposed in the second connecting rod 0022b in the mask positioning assembly 00 (i.e., the connecting rod on the left in FIG. 2 or 6), and make the end face of the boss with a larger diameter of the stepped boss 102b1 be in contact with one end, distal from the first frame 0021, of the second connecting shaft 0022b with the fixing hole 0022b1, such that the first frame 0021 and the second frame 101 are fixedly connected to each other, that is, the adapter frame 002 and the positioning assembly support frame 10 are fixedly connected to each other.

In the case that the treatment is completed, the stepped boss 102b1 may be adjusted in the axial direction X, to make the stepped boss 102b1 move along the axial direction X toward one end distal from the at least two third connecting ports 105a, and make the first frame 0021 disconnect from the second frame 101. That is, the adapter frame 002 is disconnected from the positioning assembly support frame 10, thereby facilitating the removal of the mask positioning assembly 10 from the positioning system.

Figure 15:
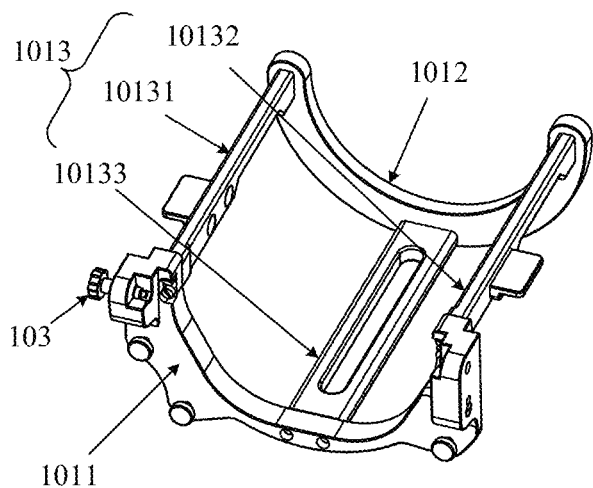
FIG. 15 is a schematic structural diagram of yet another positioning assembly support frame according to an embodiment of the present disclosure.

As an optional implementation, FIG. 15 is a schematic structural diagram of yet another positioning assembly support frame according to an embodiment of the present disclosure. The positioning system may be applied in the case of an image acquisition system including MRI equipment. As may be seen with reference to FIG. 15, the second frame 101 may include a first U-shaped frame 1011, a second U-shaped frame 1012, and a connecting assembly 1013 configured to connect the first U-shaped frame 1011 to the second U-shaped frame 1012.

Further, the above connecting assembly 1013 may include a first connecting member 10131, a second connecting member 10132, and a third connecting member 10133. One end of each of the first connecting member 10131, the second connecting member 10132, and the third connecting member 10133 is connected to the first U-shaped frame 1011, and the other end of each of the first connecting member 10131, the second connecting member 10132, and the third connecting member 10133 is connected to the second U-shaped frame 1012.

More specifically, one end of the first connecting member 10131 may be connected to one end of the first U-shaped frame 1011, and the other end of the first connecting member 10131 may be connected to one end of the second U-shaped frame 1012. One end of the second connecting member 10132 may be connected to the other end of the first U-shaped frame 1011, and the other end of the second connecting member 10132 may be connected to the other end of the second U-shaped frame 1012. One end of the third connecting member 10133 may be connected to a bottom end of the first U-shaped frame 1011, and the other end of the third connecting member 10133 may be connected to a bottom end of the second U-shaped frame 1012. The at least two third connecting ports 105a may be disposed on the first U-shaped frame 1011, and the stepped boss 102b1 may be disposed on one side, opposite to the at least two third connecting ports 105a, of the first U-shaped frame 1011.

Figure 16:
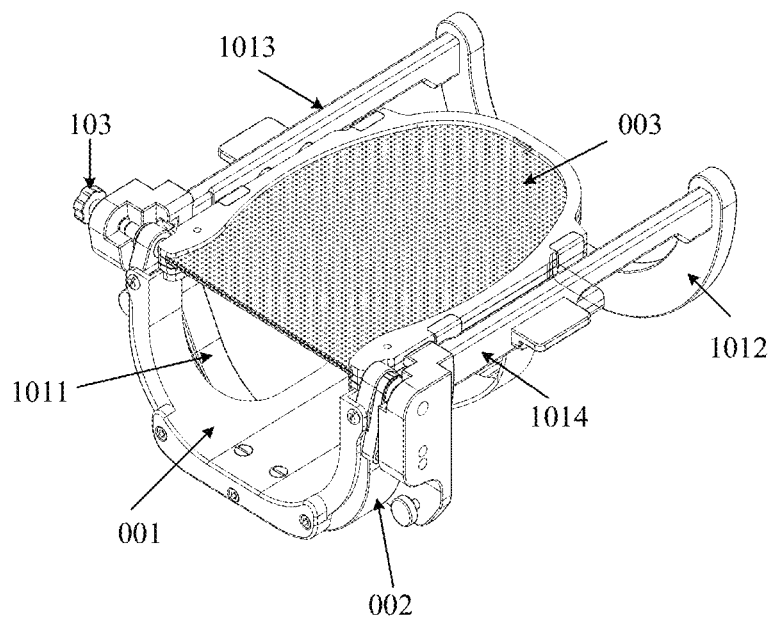
FIG. 16 is a schematic structural diagram of another positioning assembly support frame and mask positioning assembly according to an embodiment of the present disclosure.

FIG. 16 is a schematic structural diagram of another positioning assembly support frame and mask positioning assembly according to an embodiment of the present disclosure. As may be seen with reference to FIGS. 15 and 16, the positioning mask 003 in the mask positioning assembly 00 may be disposed in an area enclosed by the first U-shaped frame 1011, the second U-shaped frame 1012, the first connecting member 10131, the second connecting member 10132, and the third connecting member 10133. The first connecting member 10131, the second connecting member 10132, and the third connecting member 10133 may all be rod-shaped structures, and the first connecting member 10131, the second connecting member 10132, and the third connecting member 10133 may be connected to the first U-shaped frame 1011 and the second U-shaped frame 1012 by bolts.

As another optional implementation, the positioning system may also be applied in the case of an image acquisition system including CT equipment or in the case of a radiotherapy system including radiotherapy equipment. The second frame 101 may be a U-shaped frame.

Regarding the positioning assembly support frame 10 in FIGS. 3, 4, and 13, the positioning system may include radiotherapy equipment, that is, the positioning assembly support frame 10 shown in FIGS. 3, 4, and 13 may be applied to a radiotherapy system including radiotherapy equipment. The positioning assembly support frame 10 may include the second frame 101 and the second connecting structure 102 disposed on the second frame 101. The second frame 101 may be a U-shaped frame, and the third connecting substructure 102a, the second angle adjusting mechanism 104, and the second angle detecting mechanism 105 in the second connecting structure 102 may be disposed at one end of the U-shaped frame, wherein the third connecting substructure 102a may be a through hole, the second angle adjusting mechanism 104 may include the first connecting shaft 104a, and the second angle detecting mechanism 105 may include the at least two third connecting ports 105a. The fourth connecting substructure 102b in the second connecting structure 102 may be disposed at the other end of the U-shaped frame, wherein the fourth connecting substructure 102b may include the stepped boss 102b1.

Figure 17:
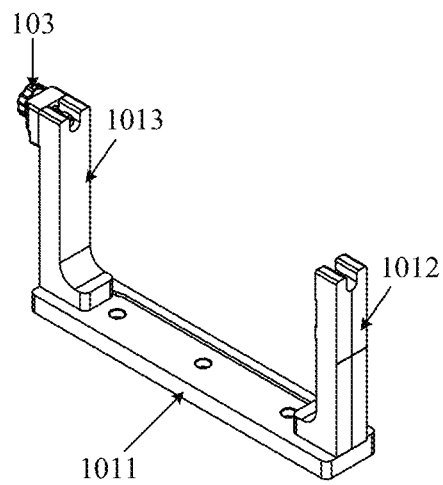
FIG. 17 is a schematic structural diagram of still another positioning assembly support frame according to an embodiment of the present disclosure.
Figure 18:
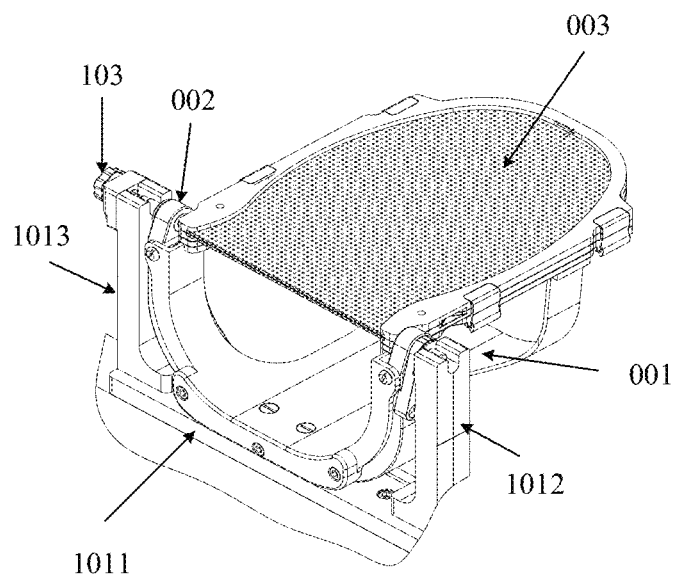
FIG. 18 is a schematic structural diagram of yet another positioning assembly support frame and mask positioning assembly according to an embodiment of the present disclosure.

FIG. 17 is a schematic structural diagram of still another positioning assembly support frame according to an embodiment of the present disclosure. FIG. 18 is a schematic structural diagram of yet still another positioning assembly support frame and mask positioning assembly according to an embodiment of the present disclosure. Regarding the positioning assembly support frame 10 shown in FIGS. 17 and 18, the positioning system may include CT equipment, that is, the positioning assembly support frame 10 shown in FIGS. 17 and 18 may be applied to an image acquisition system including CT equipment. The positioning assembly support frame 10 may include the second frame 101 and the second connecting structure 102 disposed on the second frame 101. The second frame 101 may include a first rod 1011, a second rod 1012, and a third rod 1013, which may form a U-shape structure upon being connected to each other, that is, the second frame 101 may be a U-shaped frame.

As may be seen with reference to FIG. 17, one end of the first rod 1011 may be connected to one end of the second rod 1012, and the other end of the first rod 1011 may be connected to one end of the third rod 1013. The third connecting substructure 102a, the second angle adjusting mechanism 104, and the second angle detecting mechanism 105 in the second connecting structure 102 may be disposed at the other end of the second rod 1012, wherein the third connecting substructure 102a may be a through hole or a groove, the second angle adjusting mechanism 104 may include the first connecting shaft 104a, and the second angle detecting mechanism 105 may include the at least two third connecting ports 105a. The fourth connecting substructure 102b in the second connecting structure 102 may be disposed at the other end of the third rod 1013, wherein the fourth connecting substructure 102b may include the stepped boss 102b1. The first rod 1011, the second rod 1012, and the third rod 1013 may all be columnar structures and may be connected with each other by bolts.

As may be seen with reference to FIGS. 3, 5, and 13 to 18, the stepped boss 102b1 may include two coaxial bosses with different diameters. The second frame 101 may be provided with a through hole. One end of the boss with a larger diameter of the stepped boss 102b1 is connected to the boss with a smaller diameter, and the other end of the boss with a larger diameter can pass through the through hole. The positioning assembly support frame 10 may further include the knob 103, which may be fixedly connected to the other end of the boss with a larger diameter of the stepped boss 102b1. The operator can turn the knob 103 to make the stepped boss 102b1 move along the axial direction X.

In summary, embodiments of the present disclosure provide a positioning system, which may include a patient support device, a positioning assembly support frame, and a mask positioning assembly. The positioning assembly support frame may be fixedly disposed on the patient support device, and the mask positioning assembly is applicable to different types of positioning systems, such that during quick and accurate treatment for a patient, the patient's head may be positioned using the same mask positioning assembly, which has a low cost. There is no need to frequently replace different mask positioning assemblies to adapt to different positioning systems, thereby achieving high efficiency. In addition, by using the mask positioning assembly according to the embodiments of the present disclosure to position the patient's head, the problem of poor positioning accuracy in the case that the patient is positioned using different mask positioning assemblies can be avoided, therefore a high positioning accuracy is achieved and therapeutic effect for the patient is improved.

Described above are merely optional embodiments of the present disclosure, and are not intended to limit the present disclosure. Within the spirit and principles of the disclosure, any modifications, equivalent substitutions, improvements, and the like are within the protection scope of the present disclosure.

What is claimed is:

1. A mask positioning assembly, comprising:
    a cradle frame, an adapter frame, and a positioning mask, wherein:
    the cradle frame is connected to both the adapter frame and the positioning mask; and
    the adapter frame is configured to be connected to any of positioning assembly support frames in different types of positioning systems;
    the adapter frame comprises a first frame and a first connecting structure disposed on the first frame;

a first connecting port is disposed on the first frame, wherein the first frame is connected to the cradle frame through the first connecting port; and the first connecting structure is configured to be connected to a second connecting structure on a second frame of the positioning assembly support frame, wherein the first connecting structure and the second connecting structure are detachably connected to each other.

2. The mask positioning assembly according to claim 1, wherein the different types of positioning systems comprise at least two of an image acquisition system comprising computed tomography equipment, an image acquisition system comprising magnetic resonance imaging equipment, and a radiotherapy system.

3. The mask positioning assembly according to claim 1, wherein the first connecting structure comprises a first connecting substructure and a second connecting substructure respectively disposed at two ends of the first frame, wherein the first connecting substructure is configured to be connected to a third connecting substructure of the second connecting structure, and the second connecting substructure is configured to be connected to a fourth connecting substructure of the second connecting structure, the third connecting substructure and the fourth connecting substructure being respectively disposed at two ends of the second frame.

4. The mask positioning assembly according to claim 3, wherein the first frame is capable of being locked by the connection between the third connecting substructure and the first connecting substructure and/or the connection between the fourth connecting substructure and the second connecting substructure, such that a position of the first frame is fixed relative to the second frame.

5. The mask positioning assembly according to claim 1, wherein the adapter frame further comprises a first angle adjusting mechanism and/or a first angle detecting mechanism disposed on the first frame;

wherein the first angle adjusting mechanism is configured to adjust an angle between the first frame and the second frame by cooperation with a second angle adjusting mechanism on the second frame; and wherein the first angle detecting mechanism is configured to detect the angle between the first frame and the second frame by cooperation with a second angle detecting mechanism on the second frame.

6. The mask positioning assembly according to claim 1, wherein the first frame is a U-shaped frame.

7. The mask positioning assembly according to claim 1, wherein the cradle frame comprises an arc-shaped support plate and a positioning plate connected to the arc-shaped support plate, wherein the arc-shaped support plate is connected to the adapter frame, and the positioning plate is connected to the positioning mask.

8. The mask positioning assembly according to claim 7, wherein the positioning plate is U-shaped; or the positioning plate comprises a first plate and a second plate that are arranged oppositely and not connected to each other.

9. The mask positioning assembly according to claim 1, wherein the positioning mask comprises a mask frame and a double-shell mask, wherein the mask frame comprises two mask frame members that are fixedly connected to the double-shell mask, the two mask frame members being stacked and both fixedly connected to the cradle frame.

10. The mask positioning assembly according to claim 9, wherein the mask frame member and the cradle frame are connected to each other by one or more of a pin, a buckle, and an expansion plug.

11. The mask positioning assembly according to claim 9, wherein each of the mask frame members is U-shaped; or each of the mask frame members comprises a first frame member and a second frame member that are arranged oppositely and not connected to each other.

12. A positioning system, comprising:

a patient support device, a positioning assembly support frame, and a mask positioning assembly, wherein:

the mask positioning assembly comprises: a cradle frame, an adapter frame, and a positioning mask, wherein the cradle frame is connected to both the adapter frame and the positioning mask;

and the adapter frame is configured to be connected to any of positioning assembly support frames in different types of positioning systems;

the positioning assembly support frame is fixedly disposed on the patient support device, and the mask positioning assembly is connected to the positioning assembly support frame;

the positioning assembly support frame comprises a second frame and a second connecting structure disposed on the second frame; and the second connecting structure is connected to a first connecting structure of a first frame of an adapter frame, and the second connecting structure and the first connecting structure are detachably connected to each other.

13. The positioning system according to claim 12, wherein the second connecting structure comprises a third connecting substructure and a fourth connecting substructure disposed at two ends of the second frame, wherein the third connecting substructure is configured to be connected to a first connecting substructure of the first connecting structure, and the fourth connecting substructure is configured to be connected to a second connecting substructure of the first connecting structure.

14. The positioning system according to claim 13, wherein the first frame is in a locking state by the connection between the third connecting substructure and the first connecting substructure and/or connection between the fourth connecting substructure and the second connecting substructure, such that a position of the first frame, in the locking state, is fixed relative to the second frame.

15. The positioning system according to claim 12, wherein the positioning assembly support frame further comprises a second angle adjusting mechanism and/or a second angle detecting mechanism disposed on the second frame;

wherein the second angle adjusting mechanism is configured to adjust an angle between the second frame and the first frame by cooperation with a first angle adjusting mechanism on the first frame; and wherein the second angle detecting mechanism is configured to detect the angle between the second frame and the first frame by cooperation with a first angle detecting mechanism on the first frame.

16. The positioning system according to claim 12, wherein in case that the positioning system is applied to an image acquisition system comprising magnetic resonance imaging equipment, the second frame comprises a first U-shaped frame, a second U-shaped frame, and a connecting assembly configured to connect the first U-shaped frame to the second U-shaped frame.

17. The positioning system according to claim 16, wherein the connecting assembly comprises a first connecting member, a second connecting member, and a third connecting member;

wherein one end of each of the first connecting member, the second connecting member, and the third connecting member is connected to the first U-shaped frame, and the other end of each of the first connecting member, the second connecting member, and the third connecting member is connected to the second U-shaped frame.

18. The positioning system according to claim 12, wherein in case that the positioning system is applied to an image acquisition system comprising computed tomography equipment or applied to a radiotherapy system comprising radiotherapy equipment, the second frame is a U-shaped frame.

\* \* \* \* \*